United States Patent [19]

Wu et al.

[11] Patent Number: 4,889,941

[45] Date of Patent: Dec. 26, 1989

[54] SYNTHETIC FLAVONOIDS AS INHIBITORS OF LEUKOTRIENES AND 5-LIPOXYGENASE

[75] Inventors: Edwin S. Wu; Alexander Kover, both of Rochester, N.Y.

[73] Assignee: Fisons Corporation, Rochester, N.Y.

[21] Appl. No.: 129,014

[22] Filed: Dec. 4, 1987

Related U.S. Application Data

[63] Continuation-in-part of Ser. No. 41,817, Apr. 23, 1987, abandoned.

[51] Int. Cl.$^4$ .............................................. C07D 311/30
[52] U.S. Cl. ..................................... 549/403; 546/269
[58] Field of Search ................. 549/403, 60; 514/456; 546/269

[56] References Cited

U.S. PATENT DOCUMENTS

| 4,391,821 | 7/1983 | Korbonits et al. | 514/456 |
| 4,463,176 | 7/1984 | Dennis et al. | 546/208 |
| 4,495,198 | 1/1985 | Wu | 514/456 |
| 4,501,755 | 2/1985 | Wu | 514/456 |
| 4,668,804 | 5/1987 | Wu | 549/403 |
| 4,668,805 | 5/1987 | Wu | 549/403 |

OTHER PUBLICATIONS

P. Da Re et al., *J. Med. Chem.*, vol. 15, No. 8, pp. 868–869 (1972).
Wang Ding et al., *Acta Pharm. Sinica*, 15, 253 (1980).

*Primary Examiner*—Nicky Chan
*Attorney, Agent, or Firm*—Seidel, Gonda, Lavorgna & Monaco

[57] ABSTRACT

7-[3-[(3,4-dihydroxyphenethyl)amino]-2-hydroxypropoxy]-flavone hydrobromide, and related flavonoids are disclosed to inhibit leukotrienes and 5-lipoxygenase; preferred compounds also inhibit rat anaphylaxis.

1 Claim, No Drawings

SYNTHETIC FLAVONOIDS AS INHIBITORS OF LEUKOTRIENES AND 5-LIPOXYGENASE

CROSS-REFERENCE TO RELATED APPLICATIONS

This application is a continuation-in-part of U.S. patent application Ser. No. 041,817, filed April 23, 1987, now abandoned.

BACKGROUND OF THE INVENTION

The leukotrienes (LT's) play potent roles in hypersensitivity and inflammatory reactions in various biological systems. They are formed from arachidonic acid by a pathway that requires the action of the enzyme, 5-lipoxygenase (5-LO). Leukotrienes $C_4$ ($LTC_4$), $D_4$, and $E_4$ are sulfidopeptides that dramatically constrict the pulmonary airways and small blood vessels and that are believed to play an important role in the pathophysiology of active anaphylaxis, asthma and vasospastic disease. Thus antagonists of $LTC_4$, $D_4$, $E_4$, 5-LO, and active anaphylaxis are expected to be useful as anti-allergy agents. Another leukotriene, $LTB_4$, has inflammatory properties and has been detected in exudates from human inflammatory disease including psoriasis. In addition, leukotrienes have been found to accumulate during the crisis stage of myocardial infarction. As a result, 5-LO inhibitors are expected to be useful in the treatment of inflammation, psoriasis, and myocardial infarction.

The compounds of the invention are flavonoids that are useful in the treatment of inflammation, psoriasis, and myocardial infarction as evidenced by their ability to antagonize 5-LO in an in vitro assay. They are active as anti-allergic compounds as indicated by their abilities to antagonize the effects of $LTC_4$ in vitro on guinea pig ilial tissue and to antagonize 5-LO in an in vitro assay. Preferred compounds of the invention demonstrate an additional property, the ability to inhibit edema in a rat anaphylaxis test, which is indicative of anti-allergy activity.

Antagonists of SRS-A (slow reacting substance of anaphylaxis), the main components of which are $LTC_4$, $D_4$, and $E_4$, are known but are structurally quite different from the flavonoids of the present invention. They include sodium 7-[3-(4-acetyl-3-hydroxy-2-propyl-phenoxy)-2-hydroxypropoxy]-4-oxo-8-propyl-4H-1-benzopyran-2-carboxylate (FPL 55712) and its analogs. FPL 55712, however, is a glycerol containing a nonphenyl substituted chromone moiety. German Offenlegungsschrift, DE No. 3,416,230, European Pat. No. 0108592, and U.S. Pat. Nos. 4,518,613, 4,448,729, 4,424,231, and 3,882,148 also disclose SRS-A antagonists that are aryloxyalkane carboxylic acid derivatives.

U.S. Pat. No. 4,495,198 discloses chromonoxypropanolamines with alkyl substitution on the nitrogen as antihypertensive agents and U.S. Pat. No. 4,501,755 discloses isoflavones as anti-inflammatory agents. Neither patent, however, discloses the flavonoids of this invention.

SUMMARY OF THE INVENTION

The invention is a compound of the formula (1)

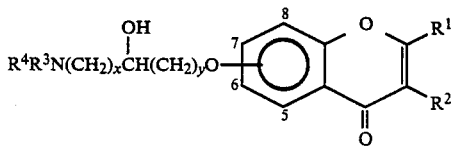

or a pharmaceutically acceptable salt thereof, wherein
$R^1$ is hydrogen or phenyl,
$R^2$ is hydrogen or phenyl,
$R^3$ is hydrogen or $C_1$-$C_5$ alkyl (straight or branched chain),
$R^4$ is either phenyl, benzyl, $R^5(CH_2)_nCH(T)(CH_2)_k$, or the heterocyclic ring

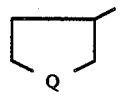

or together with $R^3$ and the nitrogen atom joining them form a 5- or 6-membered heterocyclic ring

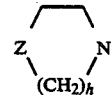

wherein
$R^5$ is either phenoxy or unsubstituted, monosubstituted, or disubstituted Ar,
Ar is either phenyl, pyridinyl, furanyl, thiophenyl, or naphthyl, each substituent of monosubstituted Ar is either OH, $C_1$-$C_5$ alkoxy (straight or branched chain), or $O(CH_2)_mCO_2R^3$, each substituent of disubstituted Ar is independently hydroxy or $C_1$-$C_5$ alkoxy,
Q is $SO_2$, S, or O,
x is a whole integer from 1 to 5,
y is a whole integer from 1 to 5,
h is a whole integer from 1 to 2,
k is a whole integer from 1 to 7,
m is a whole integer from 1 to 2,
n is a whole integer from 0 to 6,
T is either hydrogen or OH,
Z is $CH_2$, O, NH, $NCH_3$, or

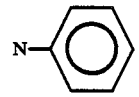

and the side chain, $R^4R^3N(CH_2)_xCH(OH)(CH_2)_yO$, is substituted at either the 5-, 6-, 7-, or 8-position of the flavone nucleus, provided that
(1) at least one of x and y is one,
(2) n plus k total no more than 7, and
(3) at least one of $R^1$ and $R^2$ is phenyl.

The compounds of the invention are expected to be useful in the treatment of inflammation, psoriasis, and myocardial infarction as evidenced by their ability to antagonize 5-LO in an in vitro assay. The compounds of the invention are expected to be active as anti-allergic compounds, as indicated by their ability to antagonize the effects of leukotriene C4 ($LTC_4$) in vitro on guinea pig ilial tissue and their ability to antagonize 5-LO in an in vitro assay. Preferred compounds of the invention additionally demonstrate the ability to inhibit edema in a rat anaphylaxis test, an ability that is indicative of anti-allergy activity. These preferred compounds are the compounds of the invention, as defined above, except that (1) Ar is not disubstituted with $C_1$-$C_5$ alkoxy when $R_3$ is $C_1$-$C_5$ alkyl.

The invention is also methods for making the compounds of formula (1) and, as to the preferred compounds referred to above, a method for using them as inhibitors of edema or anti-anaphylaxis agents.

DETAILED DESCRIPTION

Rat Anaphylaxis Test

Groups of 15-20 rats are intraperitoneally sensitized with 500 µg of bovine serum albumin-absorbed alum admixed with $2 \times 10^{10}$ killed Bordetella pertussis vaccine organisms. Fourteen days later, the paw volume is measured using a mercury plethysmometer. Immediately thereafter, the test compound suspended in about 1 ml of 1% Clearjel ("Instant Clearjel", a food grade pregelatinized starch from National Starch and Chemical Corporation, New York, N.Y.) at 100 mg/kg is administered ip and, one hour later, the right hind paw is injected subcutaneously with 100 µg of bovine serum albumin dissolved in 0.1 ml of saline. (In controls, no test compound is suspended in the Clearjel.) The paw volume is remeasured 90 minutes post antigenic challenge to determine the volume increase ($\Delta$ V) since the first measurement. The percent inhibition of edema is $$\left[ \frac{(\Delta V \text{ with test compound}) - (\Delta V \text{ with control})}{\Delta V \text{ with control}} \right] \times 100\%$$

The effect of theophylline (90 mg/kg, po) is tested as a positive control. The preferred compound in this assay is 7-[3-[(3,4-dihydroxyphenethyl)amino]-2-hydroxypropoxy]flavone hydrobromide, which caused 63% inhibition.

Test for Inhibition of LTC$_4$-Induced Guinea Pig Ilial Contractions

The evaluation of potential anti-allergic compounds for antagonism of the in vitro effects of leukotriene C4 (LTC$_4$) is conducted according to the following procedure. Guinea pig ilial strips are obtained from recently killed animals and hung in isolated tissue baths comprising a balanced solution of salts such as Krebs' solution. After allowing for one hour equilibration of the tissue in the bath, the gram tension (G.T.) on one tissue is arbitrarily set at one. LTC$_4$ (6 nanomolar concentration) is then added to the tissue bath. This induces a long, sustained contraction of the tissue that is measured on the strip chart recorder (the G.T. increases to about 2). After the LTC$_4$-induced contraction has plateaued and remains stable, increasing amounts of the test compound are added to the bath. If the compound is effective, a decrease in the G.T. ($\Delta$ G.T.) from the LTC$_4$-induced value is seen (e.g., from 2 to 1.5). The percent inhibition at each concentration is calculated according to the formula:

$$\frac{[\Delta G.T. \text{ without compound} - \Delta G.T. \text{ with compound}]}{\Delta G.T. \text{ without compound}} \times 100\%$$

Four replicate tissues are run. The preferred compound in this assay is 7-[3-[(3,4-dimethoxyphenethyl)amino]-2-hydroxypropoxy]flavone maleate which caused 52.3, 89.8, and 94% inhibition at final tissue bath concentrations of $1 \times 10^{-6}$, $5 \times 10^{-6}$, and $1 \times 10^{-5}$M, respectively.

In a minority of cases [Of 25 compounds tested, only the title compounds of Examples 11, 12 and 18 were found to be such a case.], a compound will not be testable in this assay because it is insoluble in the balanced salts solution but will be testable and active in the rat anaphylaxis test despite being administered as a suspension.

Test for Inhibition of 5-Lipoxygenase

This test is based on the procedure of Arai et al., *J. Med. Chem.*, Vol. 26, 72 (1983).

Arachidonic acid in the presence of the enzyme 5-lipoxygenase is converted to 5-hydroxy-eicosatetraenoic acid (5-HETE) through a 2-step process. To assess the activity of a test compound on 5-lipoxygenase activity, a specific concentration of the test compound is added to 1 mg/ml of arachidonic acid in the presence of the appropriate amount of 5-lipoxygenase in a solution of potassium phosphate buffer containing 1 mM CaCl$_2$ at pH 7.4. The reaction is carried out for 6 minutes at 30° C. in a total volume of 500 µl. The reaction is stopped by addition of 1M citric acid. The 5-HETE is extracted and quantitated using high performance liquid chromatography. The percent activity is calculated as follows:

$$\left[ \frac{\begin{bmatrix} \text{Amount of 5-HETE} \\ \text{produced in absence} \\ \text{of test compound} \end{bmatrix} - \begin{bmatrix} \text{Amount of 5-HETE} \\ \text{produced in presence} \\ \text{of test compound} \end{bmatrix}}{\begin{bmatrix} \text{Amount of 5-HETE produced} \\ \text{in absence of test compound} \end{bmatrix}} \right] \times 100\%$$

The preferred compound in this assay is 7-[3-[(3,4-dihydroxyphenethyl)amino]-2-hydroxypropoxy]flavone hydrobromide which had an IC$_{50}$ of about $9 \times 10^{-8}$M.

Pharmaceutically Acceptable Salts

Pharmaceutically acceptable salts are the inorganic and organic acids generally considered to be acceptable in that regard and include, but are not limited to hydrochloric, hydrobromic, sulfuric, phosphoric, acetic, lactic, succinic, fumaric, malic, maleic, tartaric, citric, benzoic, methane sulfonic and toluene sulfonic acids. In rare cases, the compound will be found to be inactive in the Rat Anaphylaxis test as such a salt but will still be active in the free base form. (Example 19 as a hydrochloric acid was the only one found so far to be such a case.)

Preparation of compounds

The compounds of formula (1) can be prepared by reacting

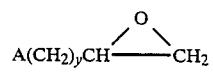

(2)

the epoxide of formula (2), wherein A is a halogen atom and y is as defined earlier provided that A is bromine or iodine when y is $>1$, with a compound of the formula

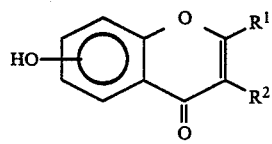

wherein R¹ and R² are the same as defined above and the hydroxyl group is substituted on the 5, 6, 7, or 8-position, in the presence of a solvent such as an alcohol of 1-4 carbon atoms or acetone, and a base such as potassium carbonate or piperidine to give a product of formula (4)

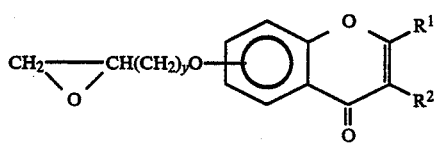

Formula (4) can also be obtained by reacting a compound of formula (3) with a ω-haloolefin A(CH₂)$_y$CH=CH₂(5), wherein A and y are the same as defined above, in the presence of a base such as sodium or potassium hydroxide, potassium carbonate, or piperidine, and a solvent such as an alcohol of 1-4 carbon atoms, acetone, dimethylformamide, or dimethylsulfoxide, to give a product of formula (6), (see Eq. 1),

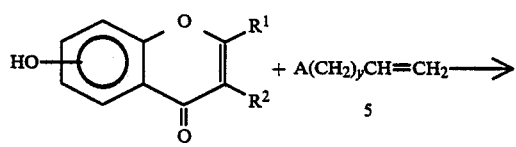

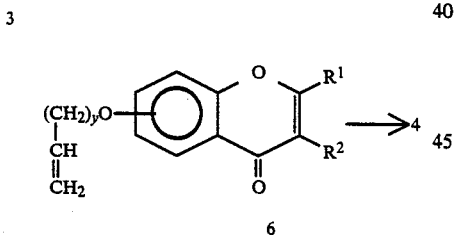

This olefin is allowed to react with peroxides such as m-chloroperbenzoic acid or peracetic acid in a suitable solvent such as chloroform, methylene chloride or acetic acid, to produce the epoxide of formula (4). Treatment of this epoxide with various amines of formula (7) or formula (8)

HNR³R⁴    7

HNR⁴R⁷    8 wherein R³ and R⁴ are the same as previously defined and R⁷ is benzyl, in an alcoholic solvent of 1-4 carbons at a suitable temperature, room temperature to 100° C., or in the presence of a Lewis acid such as triethylaluminum in CH₂Cl₂ yields a product of formula (9) or a product of formula (10) respectively.

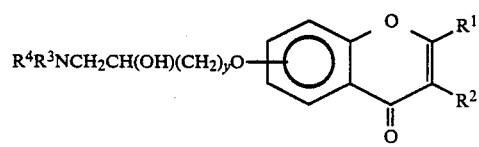

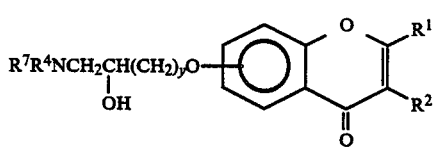

Reduction of a compound of formula 10 in the presence of palladium charcoal and hydrogen under the atmospheric pressure or higher pressure, or palladium black in methanol and formic acid or in cyclohexene or cyclohexadiene affords the product of formula (9) provided that R³ is hydrogen.

An alternative route to the preparation of the compounds of formula (1) is described in the following (Eq. 2).

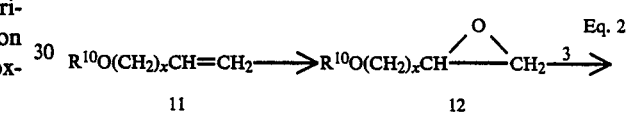

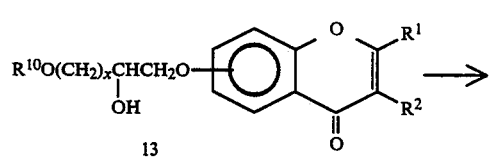

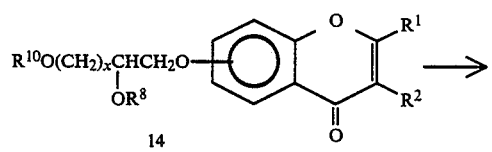

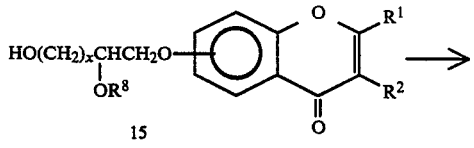

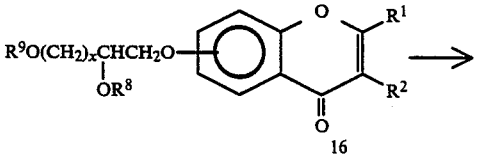

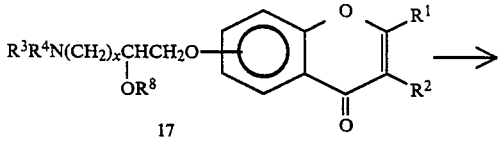

-continued

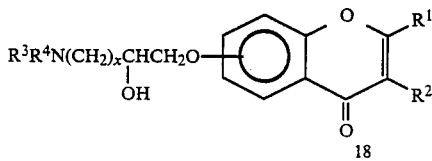

wherein $R^8$ is t-butyldimethylsilyl, (triphenylmethyl)dimethylsilyl or t-butyldiphenylsilyl and $R^9$ is methanesulfonato or p-toluenesulfonato. The ether olefin of the formula (11)

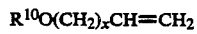

wherein $R^{10}$ is 2-tetrahydropyranyl or benzyl with 2-tetrahydropyranyl being preferred, is epoxidized, with m-chloroperbenzoic acid or peracetic acid in the presence of or the absence of a base such as potassium carbonate in methylene chloride or acetic acid at room temperature, to the epoxide of the formula (12)

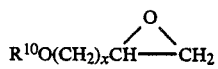

wherein $R^{10}$ and x are defined as given previously. The compounds of formula (13), wherein $R^1$, $R^2$, $R^{10}$ and x are the same as described above, are prepared from the reaction of formula (12) and formula (3) in the presence of a base such as a catalytic amount of piperidine or sodium hydroxide in aqueous ethanol at the elevated temperature of 50°–120° C. Silylation of formula (13) with various bulky or hindered silyl chlorides such as t-butyldimethylsilyl chloride, (triphenylmethyl)dimethylsilyl chloride, or t-butyl-diphenylsilyl chloride in the presence of imidazole and dimethylformamide at room temperature to 100° C. produces compounds of formula (14), wherein the definitions of $R^1$, $R^2$, $R^8$, $R^{10}$, and x are the same as given above. Using pyridinium p-toluenesulfonate in an alcoholic solvent such as methanol, ethanol, or isopropyl alcohol at the elevated temperature of 50°–100° C. if $R^{10}$ is tetrahydropyranyl or using conventional catalytic hydrogenation if $R^{10}$ is benzyl, formula (14) is selectively deprotected to a product of formula (15). Conversion of (15) to (16) is carried out reacting (15) with methanesulfonyl chloride or p-toluenesulfonyl chloride at room temperature (RT; about 25° C.) in the presence of a base such as pyridine or triethylamine and a solvent such as methylene chloride. Compounds of formula (17) are derived from the reaction of (16) with various amines of formula (7) in a polar solvent such as dimethylsulfoxide at the elevated temperature from 50°–120° C. The silylated compound (17) is desilylated to formula (18) during the preparation of the acid salt of (18). The definitions of $R^1$, $R^2$, $R^3$, $R^4$, $R^8$, $R^9$, $R^{10}$, and x for formula (13), (14), (15), (16), and (17) are the same as given previously.

EXAMPLES

The following Examples are intended to illustrate, but not limit, the invention.

EXAMPLE 1

Preparation of 7-[3-[(3,4-dimethoxyphenethyl)amino]-2-hydroxypropoxy]flavone Maleate (a) 7-(2,3-Epoxypropoxy)flavone To a solution of 82.2 g (2.06 mol) of sodium hydroxide in 585 ml of water were added 3.7 liters of isopropanol and then 490 g (2.06 mole) of 7-hydroxyflavone. To the above mixture were then added 1645 ml (20.5 mole) of epichlorohydrin and the mixture heated at 70° C. for 2 hours with stirring. The hot reaction mixture was filtered to remove dimeric by-product. The filtrate was concentrated under reduced pressure (water aspirator) at 50°–60° C. The semisolid residue was treated with 4.4 liters of refluxing isopropanol and more of the dimer filtered from the hot mixture. The clear filtrate on cooling yielded a solid. This was filtered, washed with 600 ml of isopropanol and air dried; yield 434.3 g (72%) of a tan-colored product, mp 123°–130° C. (a pure sample melts at 133°–135° C. from i-PrOH). The crude epoxide was used for further reaction.

(b) 7-[3-[(3,4-Dimethoxyphenethyl)amino]-2-hydroxypropoxy]flavone Maleate

To a suspension of 7-(2,3-epoxypropoxy)flavone (5.0 g, 17 mmol), 3,4-dimethoxyphenethylamine (6.2 g, 34 mmol), and 50 ml of ethanol was heated to a solution at 50°–60° C. in the presence of nitrogen and the reaction was then monitored by thin layer chromatography (TLC). After the reaction was complete (4 hours), the reaction mixture was filtered off (to remove insoluble materials from the crude epoxide) and cooled to room temperature. The precipitated solid was collected and washed with 95% ethanol to give a tan solid of 6.4 g of the free base (79% yield). The solid was suspended in 100 ml of hot ethanol and mixed with 1.92 g of maleic acid. The mixture was heated to a solution, filtered, and cooled to room temperature to give 5.66 g of white crystals (71%), mp 161°–163° C. (softened at 113° C.).

EXAMPLES 2–12

Following the procedure of Example 1b, except as otherwise noted, the following compounds were prepared using the specified appropriate amines and acids. Yields are expressed as the percent molar yield from 7-(2,3-epoxypropoxy)flavone.

2. 7-[3-[N-(3,4-Dimethoxyphenethyl)-N-methylamino]-2-hydroxypropoxy]flavone Maleate, N-(3,4-dimethoxyphenethyl)-N-methylamine; was used in step (b); step (b) reaction complete in 2 hours; maleic acid; mp 143°–146° C. (EtOH) 49% yield.

3. 7-[3-[(4-Methoxyphenethyl)amino]-2-hydroxypropoxy]flavone Maleate, 4-methoxyphenethylamine; maleic acid; mp 163°–165° C. (EtOH), 27% yield. 4. 7-(3-Phenethylamino-2-hydroxypropoxy)flavone Hydrochloride, phenethylamine; step (b) complete in 3 hours; hydrogen chloride; mp 223°–225° C. (EtOH), 46% yield.

5. 7-(3-Benzylamino-2-hydroxypropoxy)flavone Hydrochloride, benzylamine in step (b); hydrogen chloride instead of maleic acid in step (b); mp 233°–234° C. (MeOH—Ether), 36% yield; methanol was used as the solvent instead of ethanol.

6. 7-[3-(N-isopropyl-N-benzylamino)-2-hydroxypropoxy]flavone Hydrochloride, N-methyl-N-benzylamine; hydrogen chloride; mp 190° C. (MeOH—Ether), 33% yield; methanol was used as the solvent instead of ethanol.

7. 7-(3-Anilino-2-hydroxypropoxy)flavone Hydrochloride, 84 mmol aniline in step (b); hydrogen chloride instead of maleic acid; mp 218°–225° C. (decomposed; EtOH), 29% yield.

8. 7-[3-[(4-Phenylbutyl)amino-2-hydroxypropoxy]flavone Maleate, 4-phenylbutylamine; step (b) reaction was done for 4 hr at 60° and plus overnight at RT; maleic acid, mp 164°–166° C. (EtOH), 50% yield.

9. 7-[3-[2-(2-Thienyl)ethylamino]-2-hydroxypropoxy]flavone Maleate, 39.3 mmol 2-(2-thienyl)ethyl amine was reacted with 20.4 mmol of the epoxypropoxyflavone for 3 hr; maleic acid; mp 183° C. (EtOH; decomposed), 50% yield.

10. 7-[3-(3-Sulfolanylamino)-2-hydroxypropoxy]flavone Hydrochloride, 3-sulfolanylamine; hydrogen chloride; mp 232°–234° C. (DMF), 7% yield; methanol was used as the solvent instead of ethanol.

11. 7-[3-[3-phenoxy-2-(hydroxypropyl)amino]-2-hydroxypropoxy]flavone Hydrochloride, 3-phenoxy-2-hydroxypropylamine; hydrogen chloride; mp 209°–211° C. (MeOH), 19% yield; methanol was used as the solvent instead of ethanol.

12. 7-[3-(N-phenylpiperazinyl)-2-hydroxypropoxy]flavone, N-phenylpiperazine; mp 175°–177° C. ($CHCl_3$—MeOH), 52% yield; methanol was used as a solvent instead of ethanol.

EXAMPLE 13

Preparation of 7-[3-[(4-hydroxyphenethyl)amino]-2-hydroxypropoxy]flavone Maleate.

A suspension of 7-(2,3-epoxypropoxy)flavone (5.0 g, 17 mmol), tyramine (4.7 g, 34 mmol), and absolute ethanol (50 ml) was heated and stirred to a solution and stirred at 60° C. for 4 hours. The reaction mixture was then cooled to room temperature to give a solid (4.0 g). The solid was flash column chromatographed through silica gel eluting with isopropanol-ethanol-acetic acid (i-PrOH—EtOH—HOAc; 20:10:1) initially and then EtOH—HOAc (20:1). The white solid obtained from evaporation of pure fractions was treated with 50 ml of hot ethanol and maleic acid (1 g), filtered, and left at RT to crystallize out. The crystals were collected, dissolved in hot methanol (50 ml), and diluted with 100 ml of ethanol to give the maleate as white crystals (2.50 g); mp 188° C. (decomp); 27% yield.

EXAMPLE 14

Preparation of 7-[3-[(3,4-Dihydroxyphenethyl)amino]-2-hydroxypropoxy]flavone Hydrobromide To a suspension of 7-[3-[(3,4-dimethoxyphenethyl)amino]-2-hydroxypropoxy]flavone, Example 3, (5.3 g, 11.1 mmol) in dry methylene chloride (100 ml) under nitrogen at −78° C. was slowly added boron tribromide (6.3 ml, 16.7 g, 66.9 mmol) via a syringe. The cooling bath was then removed and the suspension was stirred for 1 hour. The reaction mixture was carefully decomposed by addition of a sufficient amount of water to precipitate out a brown gum leaving a clear supernatant. The liquid was decanted and the residue was washed with three portions of water. The gum was dissolved in hot isopropanol, filtered, and left to precipitate overnight. The brown solid obtained was heated in acetic acid (50 ml) and water (10 ml) to give a dark brown solution which was then treated with a few crystals of sodium dithionite to give a light tan solution. In the presence of nitrogen, the product was crystallized from the solution; 1.9 g (33%), mp 207°–210° C. (decomp).

EXAMPLE 15

Preparation of 7-[3-[4-(Carbomethoxymethoxy)-phenethylamino]-2-hydroxypropoxy]flavone Maleate 7-[3-[(4-Hydroxyphenethyl)amino]-2-hydroxypropoxy]flavone (10.8 g, 25.1 mmol), Example 13, was dissolved in 20 ml of warm DMF at 50°–60° C. and then cooled to −20° C. Sodium hydride (1.2 g, 0.0251 mmol) was added portionwise to the above cooled solution, stirred at −20° C. for 1 hour, and then cooled to −40° C. Methyl bromoacetate (3.8 g, 25.1 mmol) was added dropwise to the stirred solution and the reaction mixture was kept at this temperature for 2 hours and at RT overnight. The reaction was poured into 1.5 l of water, the water decanted, and the residue washed with two portions of water. The gummy material was then purified by flash column chromatography, eluting with $CHCl_3$—MeOH (20:1). The isolated material (2.7 g) was recrystallized from methanol, and the crystallized solid was treated with 30 ml of ethanol and maleic acid (0.3 g) to give the title compound as white crystals, mp 154°–156° C., 1.5 g (10% yield).

EXAMPLE 16

Preparation of 7-[3-[[4-(Carboxymethoxy)phenethylamino]-2-hydroxypropoxy]flavone Maleate A suspension of Example 15 (1.9 g, 3.77 mmol) in methanol-water (2:1) was made strongly basic with 5% aqueous NaOH and stirred at room temperature for 1.5 hours followed by gentle warming to complete the hydrolysis. The solution was then acidified to pH 4–5 with conc. HCl, the precipitated gum was washed with water and taken up in hot methanol. The suspension was made strongly acidic with conc. HCl resulting in a solution which was left to crystallize. The precipitated solid showed the presence of a substantial amount of the starting ester, presumed to be formed during the purification step. This material was redissolved in aqueous NaOH over 1 hour and acidified to pH 5, the precipitated gum was washed with 3 portions of water, taken up in hot methanol and treated with 3 equivalents of maleic acid. The presence of the reformed ester was again shown by TLC chloroform-methanol-acetic acid 15:5:1). The solid was washed successively with hot isopropanol then hot ethanol. The white solid thus isolated proved to be the free base of the desired compound. Suspension of the material in 75 ml 95% ethanol and treatment with enough maleic acid to give a clear solution followed by crystallization afforded the title compound in 1.44 g (63%) recovery, mp 170° C. (d) with softening at 135° C.

EXAMPLE 17

Preparation of 7-[3-[(3-Nicotinylpropyl)amino]-2-hydroxypropoxy]flavone (a) N-(3-Nicotinylpropyl)benzylamine To a solution of 3-nicotinyl-1-propanol (50.0 g, 365 mmol) and triethylamine (110 g, 1.09 mol) in methylene chloride (500 ml) at 0° C. was added dropwise methanesulfonyl chloride (83.5 g, 7.29 mmol). The solution was stirred at 0° C. for 1 hour and then RT for 1 hour, and the excess of methanesulfonyl chloride was carefully decomposed with ice-water. The organic layer was separated and washed with water (twice). The aqueous layer and washings were combined, basified with 50% aqueous sodium hydroxide, and extracted with methylene chloride (3 times). The methylene chloride extracts were combined, washed with saturated brine solution, dried ($MgSO_4$), and evaporated to give 72.0 g (92% yield) of the mesylate which was used immediately for the further reaction.

A solution of the mesylate (72.0 g, 334 mmol) and benzylamine (179.2 g, 1.6 mol) in DMSO (300 ml) was stirred at RT overnight. The reaction mixture was poured into 2 l of water and extracted with ethyl acetate (three times). The extracts were dried with MgSO$_4$, thus yielding 75 g of a red oil after evaporation of benzylamine. The oil was used directly for the next reaction without further purification.

(b) 7-[3-[N-benzyl,N-(3-nicotinylpropyl)amino]-2-hydroxypropoxy]flavone

A mixture of 7-(2,3-epoxypropoxy)flavone (15 g, 51.0 mmol) and N-(3-nicotinylpropyl)benzylamine (22.5 g, 100 mmol) in ethanol (150 ml) was heated at 60° C. for 3 hours. The ethanol was then evaporated and the residue was washed with cyclohexane (three times) to remove the excess amine. The remaining residue was then extracted with ethyl acetate (twice), and the extracts were evaporated to give a red syrup. Purification of the red syrup by flash column chromatography eluting with EtOAc—MeOH (20:1) gave 8.0 g of a yellow syrup, 30% yield, which is stored in the refrigerator and used for the further reaction.

(c) 7-[3-[(3-Nicotinylpropyl)amino]-2-hydroxypropoxy]flavone

A suspension of 7-[3-[N-benzyl,N-(3-nicotinylpropyl)amino]-2-hydroxypropoxy]flavone (4.50 g, 8.64 mmol), Example 17b, palladium black (0.1 g), cyclohexene (30 ml), and acetic acid (30 ml) was refluxed for 6 hours. The solvent was evaporated to give a residue which was dissolved in water and washed with chloroform (twice) to remove impurities. The aqueous solution was basified with 2.5N NaOH and then extracted with methylene chloride several times. The extracts were washed with water, dried (MgSO$_4$), and evaporated to afford a yellow solid of 2.9 g. Recrystallization from isopropyl alcohol gave light yellow crystals (2.0 g; 54% yield), mp 116°–119° C.

EXAMPLES 18–21

The following 3-phenylflavone analogs were prepared from the reaction of 3-phenyl-7-(2,3-epoxypropoxy)flavone (U.S. Pat. No. 4,495,198) with appropriate amines using the method of Example 1b. Yield was based on the starting epoxide.

18. 3-Phenyl-7-(3-phenethylamino-2-hydroxypropoxy)flavone, mp 160°–162° C. (MeOH), 48% yield; methanol was used as the solvent instead of ethanol; phenethylamine was used.

19. 3-Phenyl-7-(3-anilino-2-hydroxypropoxy)flavone, aniline; mp 158°–160° C. (i-PrOH), 77% yield; methanol was used as the solvent.

20. 3-Phenyl-7-(3-piperidino-2-hydroxypropoxy)flavone, piperidine; mp 148°–148.5° C. (i-PrOH), 90% yield; isopropyl alcohol was used as the solvent.

21. 3-Phenyl-7-(3-morpholino-2-hydroxypropoxy)flavone, morpholine; mp 161°–162° C. (i-PrOH), 93% yield; isopropyl alcohol was used as the solvent.

EXAMPLE 22

Preparation of 7-(3-Phenethylamino-2-hydroxypropoxy)isoflavone Maleate

The title compound was prepared from the reaction of 7-(2,3-epoxypropoxy)isoflavone (U.S. Pat. No. 4,501,755) with 84 mmol phenethylamine but otherwise using the same procedure as described in the synthesis of Example 1b; mp 145°–147° C. (EtOH), 50% yield.

EXAMPLE 23

Preparation of 8-(3-Phenethylamino-2-hydroxypropoxy)isoflavone (a) 8-(2,3-Epoxypropoxy)isoflavone Following the procedure of Example 1a, the title compound was prepared from the reaction of 8-hydroxyisoflavone with epichlorohydrin, mp 141°–143° C. (i-PrOH).

(b) 8-[3-(N-benzyl-N-phenethylamino)-2-hydroxypropoxy]isoflavone hydrochloride

To a cold (0° C.) solution of N-benzylphenethylamine (3.23 g, 15.3 mmol) in CH$_2$Cl$_2$ (45 ml) a solution of triethylaluminum (8.1 ml, 1.9M in toluene, 15.3 mmol) was added dropwise under a N$_2$ atmosphere. The solution was stirred at room temperature for 30 min, and 8-(2,3-epoxypropoxy)isoflavone (4.5 g, 15.3 mmol) was added in one portion. Stirring was continued for 1 hr, and the reaction mixture was then decomposed by careful addition of sat. aqueous NH$_4$Cl (rapid evolution of ethane occurred). The two phase mixture was stirred for 3 hr, the emulsion diluted with water, the layers separated, and the aqueous suspension extracted with two portions of CH$_2$Cl$_2$. The combined organic solutions were washed with one portion of water and dried (MgSO$_4$). The solvent was evaporated to afford a residue. The residue was purified by flash chromatography through NH$_3$ deactivated silica gel eluting with CH$_2$—Cl$_2$—Ether 40:1 to yield 6.77 g (87.5% yield) of purified pale yellow syrup. A 2.8 g portion of the material was dissolved in ether and acidified with ethanol saturated with HCl. The precipitated white solid was recrystallized from methanol giving 1.6 g pure material mp 203°–205° C.

(c) 8-(3-Phenethylamino-2-hydroxypropoxy)isoflavone hydrochloride

A suspension of 8-[3-(N-benzyl-N-phenethylamino)-2-hydroxypropoxy]isoflavone (4.63 g, 9.16 mmol), Example 23b, palladium hydroxide on carbon (0.4 g), cyclohexene (25 ml), and acetic acid (25 ml) was heated at reflux for 30 min. and cooled. The catalyst was filtered off and the solvent was evaporated. The residue was dissolved in isopropyl alcohol and acidified with ethanol saturated with HCl to afford a white solid which was recrystallized from 90 ml of methanol giving 2.38 g (57.5% yield) of the title compound mp 195°–197°.

EXAMPLE 24

Preparation of 5-(3-Phenethylamino-2-hydroxypropoxy)flavone Hydrochloride (a) 5-(2,3-Epoxypropoxy)flavone The epoxide was prepared from 5-hydroxyflavone and epichlorohydrin, as described for the synthesis of Example 1a, mp 134°–135° C. (i-PrOH).

(b) 5-(3-Phenethylamino-2-hydroxypropoxy)flavone Hydrochloride

Following the procedure of Example 1b, the hydrochloride was obtained from the reaction of Example 24a and phenethylamine followed by HCl/EtOH in 35% yield, mp 223°–225° C. (i-PrOH-CH$_2$Cl$_2$).

EXAMPLE 25

Preparation of 6-(3-Phenethylamino-2-hydroxypropoxy)flavone Maleate

The title compound was prepared from the reaction of 11.6 mmol 6-(2,3-epoxypropoxy)flavone (U.S. Pat. No. 4,495,198) with 57 mmol phenethylamine but otherwise following the procedure of Example 1b; mp 162°–163° C. (EtOH), 68% yield.

EXAMPLE 26

Preparation of 8-(3-Phenethylamino-2-hydroxypropoxy)flavone Maleate (a) 8-(2,3-Epoxypropoxy)flavone Following the procedure of Example 1a, the epoxide was synthesized from 8-hydroxyflavone and epichlorohydrin.

(b) 8-(3-Phenethylamino-2-hydroxypropoxy)flavone Maleate

The maleate was prepared from 11.6 mmol of the title compound of Example 26a and 57 mmol phenethylamine, but otherwise following the procedure of Example 1b, in 68% yield, mp 162°–163° C. (EtOH).

EXAMPLE 27

Preparation of 7-[3-(8-Phenyloctylamino)-2-hydroxypropoxy]flavone Maleate (a) N-(8-Phenyloctyl)benzylamine A suspension of 8-phenyloctyl chloride (10.1 g, 44.7 mmol), benzylamine (47.9 g, 44.7 mmol), and anhydrous powdered potassium carbonate in DMF (180 ml) refluxed overnight and cooled to RT. DMF was then evaporated under reduced pressure and water (300 ml) was added to the residue. The oil layer was separated, and the aqueous layer was further extracted with ether (2×150 ml). The ether extracts were evaporated and then combined with the oil layer. The combined oil was diluted with water (250 ml) and acidified with 10% HCl solution to give a white precipitate, 16 g, which was suspended in water (150 ml) and basified with ammonium hydroxide. After being stirred for 10 minutes, most of the white solid went into the solution. Ether (100 ml) was added and stirred for an additional 30 minutes. Organic layer was separated and the aqueous layer was extracted with ether (150 ml×2). Ether extracts were combined, washed with water and saturated brine solution, and dried (MgSO$_4$), thus giving a light yellow oil of 11.90 g (90% yield).

(b) 7-[3-[N-Benzyl,N-(8-phenyloctyl)amino]-2-hydroxypropoxy]flavone

A suspension of 7-(2,3-epoxypropoxy)flavone (12.47 g, 42.3 mmol) and the secondary amine of Example 27a (11.92 g, 40.3 mmol) in methanol (84 ml) was heated at reflux for 3 hours and cooled. Evaporation of methanol afforded 24.6 g of a viscous liquid; the crude yield: 104%. The material was used directly for the next reaction without further purification.

(c) 7-[3-(8-Phenyloctylamino)-2-hydroxypropoxy]flavone Maleate

A solution of Example 27b (16.60 g, 28 mmol) in 5% HCO$_2$H/MeOH (130 ml) was slowly added to a suspension of 0.80 g of palladium black in 20 ml of 5% HCO$_2$H/MeOH and the resulting mixture was stirred under nitrogen for 4 hours. Pd black was filtered off in the presence of nitrogen and the filtrate was evaporated to give a sticky solid. Recrystallization of the solid from isopropyl alcohol twice afforded white prisms, mp 136°–138° C., of 7.50 g (56% yield from the epoxide). The free base was converted into the maleate salt following the procedure of Example 1b; mp 146°–148° C. (MeOH-i-PrOH), 62% yield (based from the free base) or 35% yield (based from the epoxide).

EXAMPLE 28

Preparation of 7-[5-(phenethylamino)-4-hydroxypentoxy]flavone Maleate (a) 7-(4-Pentenoxy)flavone A yellow suspension of 7-hydroxyflavone (25.66 g, 0.108 mol), 5-bromo-1-pentene (17.88 g, 14.2 ml, 0.12 mol), and anhydrous, powdered potassium carbonate (30.40 g, 0.22 mol) in acetone (500 ml) was stirred and heated at reflux for 24 hours. The tlc (thin layer chromatography), on silica gel eluted with 20% of hexane in ether, indicated that the reaction was incomplete. Additional 1.5 ml of 5-bromo-1-pentene was added and refluxing was continued for 6 hours and cooled. The solid was filtered and the filtrate was evaporated under vacuum to give a yellow solid 32.63 g, 97% yield. Recrystallization from isopropyl alcohol gave white crystals, mp 104.5°–106° C.; 55% yield (pure).

(b) 7-(4,5-Epoxypentoxy)flavone (i) A solution of m-chloroperbenzoic acid (5.17 g, 24 mmol) in 45 ml of CH$_2$Cl$_2$ was added slowly to a solution of the olefin (5.75 g, 18.8 mmol), Example 28a, in 25 ml of CH$_2$Cl$_2$ at 0° C. After the addition, the reaction mixture was allowed to warm up to RT and stirred for 18 hours. The solid formed was filtered off and the filtrate was washed with 1N NaOH, water, and a saturated brine solution, and dried (MgSO$_4$), thus giving 5.44 g of a solid. The epoxide was then purified by flash column chromatography followed by recrystallization from isopropyl alcohol to give white crystals, mp 110.5°–112° C.; 2.32 g, 38% yield (pure).

(ii) An alternative synthesis of this epoxide is described in the following. In the presence of nitrogen, a mixture of 7-hydroxyflavone (1.0 g, 4.2 mmol), 5-bromo-1,2-epoxypentane (1.0 g, 6.1 mmol), which was prepared from the epoxidation of 5-bromo-1-pentene with m-chloroperbenzoic acid following the procedure of Example 28(b)(i), and potassium carbonate (1.16 g, 8.4 mmol) in acetone (25 ml) was stirred and heated at reflux for 24 hours. The suspension was filtered and the filtrate was then evaporated to give a white solid of 1.31 g (97% crude yield), mp 105°–109° C.

(c) 7-[5-(Phenethylamino)-4-hydroxypentoxy]flavone Maleate

Using the procedure of Example 1b, the maleate was isolated as white crystals, mp 145°–147° C. (EtOH—CH$_2$Cl$_2$), 35% yield.

EXAMPLE 29

Preparation of 7-[5-(Phenethylamino)-2-hydroxypentoxy]flavone Maleate (a) 2-(4-Penten-1-oxy)tetrahydropyran Concentrated HCl (0.03 ml) was added dropwise over 25 minutes (slightly exothermic) to a solution of dihydropyran (5.37 g, 64 mmol) and 4-penten-1-ol (5.0 g, 58 mmol) while stirring. At RT the reaction mixture was stirred for two hours. The solution was washed with a saturated sodium carbonate solution and dried over anhydrous potassium carbonate, thus affording 8.6 g (87% yield) of a light yellow oil.

(b) 2-(4,5-Epoxypent-1-oxy)tetrahydropyran

Following the procedure of Example 28(b)i, the epoxide was prepared as a clear liquid, 88% crude yield.

(c) 7-[5-(2-Tetrahydropyranyloxy)-2-hydroxypentoxy]flavone

A solid mixture of 7-hydroxyflavone (32.0 g, 0.134 mol), piperidine (0.5 ml), and 2-(4,5-epoxypent-1-oxy)-tetrahydropyran (50 g, 0.268 mol) was stirred and heated under nitrogen at 100° C. for 14 hours; it became a stirrable mixture after 6 hours heating at 100° C. The cooled reaction mixture was purified through a pad of silica gel eluting with CH$_2$Cl$_2$ initially and then CH$_2$Cl$_2$—EtOAc (1:1). The resulting solid was stirred with ether and filtered, giving 43.9 g (77% crude yield) of an off-white solid; pure white crystals, mp 110°–112° C., were obtained from recrystallization from toluene.

(d) 7-[5-(2-Tetrahydropyranyloxy)-2-[(t-butyldimethylsilyl)oxy]pentoxy]flavone

A solution of the tetrahydropyran ether (1.0 g, 2.36 mmol), Example 29c, t-butyldimethylsilyl chloride (0.40 g, 2.83 mmol), and imidazole (0.40 g, 5.89 mmol) in DMF (5 ml) was stirred under nitrogen overnight at RT. The resulting suspension was diluted with water. The white solid was collected and washed with water to remove imidazole; 1.2 g (92% crude yield); mp 138°–145° C. (i-PrOH).

(e) 7-[5-Hydroxy-2-[(t-butyldimethylsilyl)oxy]pentoxy]flavone

A suspension of Example 29d (54.0 g, 0.10 mol) and pyridinium p-toluenesulfonate (2.5 g, 10.0 mmol) in absolute ethanol (250 ml) was stirred and heated under nitrogen at 55° C. for 8 hours and cooled. Evaporation of the solvent gave a residue which was dissolved in methylene chloride. The solution was washed with water twice and a saturated brine solution and dried (MgSO$_4$). Evaporation of the solvent gave a yellow residue which was purified through a pad of silica gel eluting with CH$_2$Cl$_2$—EtOAc (4:1) initially and then CH$_2$Cl$_2$—EtOAc (2:1). This process yielded an off-white solid (31.4 g, 69% yield), mp 124°–125° C.

(f) 7-[5-Methanesulfonato-2-[(t-butyldimethylsilyl)oxy]pentoxy]flavone

To a stirred solution of the silyl alcohol (29.0 g, 63.8 mmol), Example 29e, and triethylamine (19.4 g, 191 mmol) in methylene chloride (180 ml) under nitrogen at 0° C., methanesulfonyl chloride (14.6 g, 127 mmol) was dropwise added. The solution was stirred at 0° C. for 1 hour and then at RT for ½ hour. The excess of methanesulfonyl chloride was decomposed by addition of ice-water. The organic layer was separated, washed with water twice and a saturated brine solution, and dried (MgSO$_4$), thus giving 29.97 g (88% crude yield) of a yellow solid.

(g) 7-[5-(Phenethylamino)-2-[(t-butyldimethylsilyl)oxy]pentoxy]flavone

A stirred solution of mesylate (28.96 g, 55.3 mmol), Example 29f, and phenethylamine (33.5 g, 276 mmol) in dry DMSO (150 ml) was heated at 60°–70° C. under nitrogen for 2 hours. The resulting yellow suspension was poured into ice-water and then stirred for ½ hour at RT. The light yellow solid was collected and washed with water. The solid was dissolved in EtOH (200 ml) and precipitated out by pouring into 600 ml of water affording 29.5 g (96% crude) of a yellow solid. The product was purified by flash chromatography, eluting with ammoniated CH$_2$Cl$_2$—MeOH (20:1), recrystallized from cyclohexane, chromatographed (CH$_2$Cl$_2$—MeOH, 20:1), and recrystallized from cyclohexane; mp 89°–91° C., 48% yield.

(h) 7-[5-(Phenethylamino)-2-hydroxypentoxy]flavone Maleate

A stirred solution of the silyl amine (10.0 g, 17.9 mmol) Example 29 g, and maleic acid (8.3 g, 71.6 mmol) in 95% ethanol was heated at reflux for 14 hours and cooled. The solvent was evaporated, the syrup was washed with 3 portions of ether, triturated with hot ethyl acetate, the resulting beige solid was washed with isopropanol and recrystallized from isopropanol affording 6.14 g (61.3% yield) of a white solid. The material was washed successively with hot CH$_2$Cl$_2$ (50 ml then 90 ml) giving 5.51 g (55% yield) of a white solid, mp 149°–151° C.

EXAMPLE 30

Preparation of 8-[3-(N-benzyl-N-propylamino)-2-hydroxypropoxy]isoflavone p-toluenesulfonate Following the procedure of Example 23b, with 1.5 hr reaction time, the free base of the title compound was prepared in 84.3% yield from the reaction of Example 23a with N-benzylpropylamine. Treatment of an ether solution with a saturated solution of p-toluenesulfonic acid in ether and recrystallization from ethyl acetate gave a white solid in 84% recovery mp 155°–160° C.

What is claimed is:

1. The compound 7-[3-[(3,4-dihydroxyphenethyl)amino]-2-hydroxypropoxy]flavone hydrobromide.

* * * * *